United States Patent
Fowst et al.

(10) Patent No.: US 7,399,748 B2
(45) Date of Patent: Jul. 15, 2008

(54) ANTITUMOR THERAPY COMPRISING DISTAMYCIN DERIVATIVES

(75) Inventors: Camilla Fowst, Milan (IT); Franzanne Vreeland, Martinsville, NJ (US); Maria Cristina Rosa Geroni, Milan (IT)

(73) Assignee: Nerviano Medical Sciences S.r.l., Milan (IT)

( * ) Notice: Subject to any disclaimer, the term of this patent is extended or adjusted under 35 U.S.C. 154(b) by 627 days.

(21) Appl. No.: 10/381,272

(22) PCT Filed: Sep. 21, 2001

(86) PCT No.: PCT/EP01/10988

§ 371 (c)(1),
(2), (4) Date: Jun. 24, 2003

(87) PCT Pub. No.: WO02/28389

PCT Pub. Date: Apr. 11, 2002

(65) Prior Publication Data

US 2004/0006023 A1  Jan. 8, 2004

(51) Int. Cl.
*A61K 31/40* (2006.01)
*C07D 207/34* (2006.01)

(52) U.S. Cl. .......... 514/18; 514/428; 514/422; 514/408; 544/333; 548/524; 548/518; 548/314.7

(58) Field of Classification Search .......... 514/18, 514/428, 422, 408; 544/333; 548/524, 518, 548/314.7
See application file for complete search history.

(56) References Cited

U.S. PATENT DOCUMENTS 6,576,612 B1 * 6/2003 Fowst et al. .......... 514/18

FOREIGN PATENT DOCUMENTS

| EP | 0 388 948 A | 9/1990 |
| WO | WO 98 04524 A | 2/1998 |
| WO | WO 99 50265 A | 10/1999 |
| WO | WO 01 40181 A | 6/2001 |

* cited by examiner

*Primary Examiner*—Chih-Min Kam
(74) *Attorney, Agent, or Firm*—Scully, Scott, Murphy & Presser, P.C.

(57) ABSTRACT

The present invention relates to an administration schedule comprising the intravenous administration of a α-halogenacryloyl distamycin derivative, or a pharmaceutically acceptable salt thereof. The above administration allows the treatment of a variety of tumors in mammals.

2 Claims, No Drawings

ANTITUMOR THERAPY COMPRISING DISTAMYCIN DERIVATIVES

This application is a 371 of PCT/EP01/10988, filed Sep. 21, 2001, which claims priority of U.S. application Ser. No. 09/676,770, filed Oct. 2, 2000, now U.S. Pat. No. 6,576,612.

The present invention relates, in general, to the filed of cancer treatment and, more in particular, it relates to an antitumor therapy comprising the administration of α-bromo- and α-chloro-acryloyl distamycin derivatives.

Distamycin A is an antibiotic substance with antiviral and antiprotozoal activity, having a polypyrrole framework [Nature 203: 1064 (1964); J. Med. Chem. 32: 774-778 (1989)]. Several analogous of distamycin A, hereinafter shortly referred to as distamycin derivatives, are known in the art as cytotoxic agents useful in antitumor therapy.

The international patent application WO 98/04524, in the name of the applicant itself and herewith incorporated by reference, discloses acryloyl distamycin derivatives wherein the amidino moiety of distamycin is optionally replaced by nitrogen-containing ending groups such as, for instance, cyanamidino, N-methylamidino, guanidino, carbamoyl, amidoxime, cyano and the like.

Herewith provided is a medicament comprising the above α-halogen-acryloyl-distamycin derivatives, to be used in antitumor therapy, characterised in that the medicament is conveniently administered according to a particular dosage and schedule regimen which allow an efficacious treatment of tumors.

Therefore, a first object of the present invention is the use of a α-halogen-acryloyl distamycin derivative of formula (I)

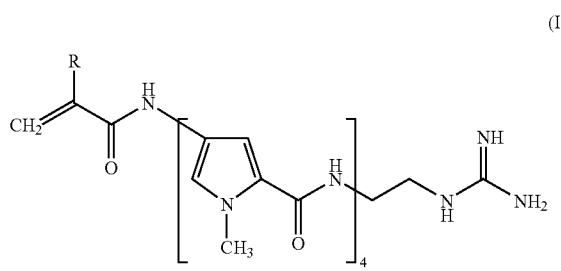

(I)

wherein:
R is a bromine or chlorine atom;
or a pharmaceutically acceptable salt thereof;
in the preparation of a medicament for the treatment of tumors by a schedule comprising the intravenous infusion of the medicament as a single administration every three or four weeks in an amount of from about 0.85 mg/M$^2$ to about 20 mg/m$^2$ of body surface area, or weekly for three consecutive weeks every four or five weeks in an amount of from about 0.3 mg/m$^2$/week to about 7 mg/m$^2$/week.

The present invention includes within its scope the use of all the possible isomers covered by the compounds of formula (I), both considered separately or in admixture, as well as the metabolites and the pharmaceutically acceptable bio-precursors, otherwise known as pro-drugs, of the compounds of formula (I).

Pharmaceutically acceptable salts of the compounds of formula (I) are those with pharmaceutically acceptable inorganic or organic acids such as, for instance, hydrochloric, hydrobromic, sulphuric, nitric, acetic, propionic, succinic, malonic, citric, tartaric, methanesulfonic, p-toluenesulfonic and the like.

Specific examples of the compounds of formula (I) according to the present invention, optionally in the form of pharmaceutically acceptable salts, preferably with hydrochloric acid, are:

N-(5-{[(5-{[(5-{[(2-{[amino(imino)methyl]amino} ethyl)amino]carbonyl}-1-methyl-1H-pyrrol-3-yl)amino] carbonyl}-1-methyl-1H-pyrrol-3-yl)amino] carbonyl}-1-methyl-1H-pyrrol-3-yl)-4-[(2-bromoacryloyl)amino]-11-methyl-1H-pyrrole-2-carboxamide hydrochloride (internal code PNU 166196); and N-(5-{[(5-{[(5-{[(2-{[amino(imino)methyl]amino}ethyl)amino]carbonyl}-1H-methyl-1H-pyrrol-3-yl)amino]carbonyl}-1-methyl-1H-pyrrol-3-yl)amino] carbonyl}-1-methyl-1H-pyrrol-3-yl)-4-[(2-chloroacryloyl)amino]-1-methyl-1H-pyrrole-2-carboxamide hydrochloride.

According to a preferred embodiment of the invention, herewith provided is the use of the compound of formula (I) wherein R is a bromine atom, that is to say the compound of formula (I) formerly indicated as PNU 166196.

The above compounds are known or easily prepared according to known methods as reported, for instance, in the aforementioned international patent application WO 98/04524, herewith incorporated by reference.

A further aspect of the present invention is to provide a method of treating a mammal, including humans, suffering from tumor, comprising administering the distamycin derivatives of formula (I) to said mammal, by intravenous infusion as a single administration every three or four weeks in an amount of from about 0.85 mg/m$^2$ to about 20 mg/m$^2$ of body surface area, or weekly for three consecutive weeks every four or five weeks in an amount of from about 0.3 mg/m$^2$/week to about 7 mg/m$^2$/week.

The exact dosage range will certainly depend form several factors including, for instance, the age, weight and conditions of the patient being treated.

The distamycin derivatives of formula (I) are preferably administered as an intravenous infusion, for instance in about 10 minutes and by using a programmable continuous infusion pump or intravenous infusion bags.

The present administration regimen is particularly effective against a variety of tumors including, for instance, solid tumors such as gastrointestinal tumors, e.g. colorectal cancer, gastro-esophageal cancer, cancer of liver and biliary tract and pancreatic cancer; prostatic cancer; testicular cancer; lung cancer; breast cancer; malignant melanoma; ovarian cancer; uterine cancer including cervical cancer; cancer of the head and neck; bladder cancer; sarcomas and osteosarcoma; Kaposi sarcoma including AIDS-related Kaposi sarcoma; renal carcinoma; hematopoietic malignant tumors such as leukemia and lymphoma, including AIDS-related lymphomas.

As formerly indicated, the compounds of formula (I) are used in the preparation of a medicament, in the form of a pharmaceutical composition, for use in the treatment of tumors.

The pharmaceutical compositions may contain an effective amount of a compound of formula (I), as the active ingredient, in association with one or more pharmaceutically acceptable carriers and/or excipients and are usually prepared following conventional methods known in the art.

As an example, solutions for intravenous injection or infusion may contain sterile water as a carrier or, preferably, they may be in the form of sterile aqueous isotonic saline solutions.

The compounds of formula (I) may also be supplied as units of freeze-dried powder for injection containing a proper amount of active ingredient, to be reconstituted before use.

In addition, the compounds of formula (I) or the pharmaceutically acceptable salts thereof may be administered according to the schedule treatment above indicated, optionally with other antitumor agents, as a combined preparation for simultaneous, separate or sequential use in anticancer therapy.

The above additional antitumor agents include, for instance, alkylating agents, topoisomerase I and II inhibitors, antimicrotubule agents and antimetabolites.

As an example, specific antitumor agents are mustards such as melphalan, chlorambucil, mechlorethamine, cyclophosphamide, ifosfamide and busulfan; nitrosoureas such as carmustine, lormustine, semustine and fotemustine; tetrazines such as dacarbazine and temozolomide; aziridines such as thiotepa and mitomycin C; platinum derivatives such as cisplatin, carboplatin, oxaliplatin, nedaplatin and lobaplatin; camptothecin derivatives such as CPT-11, Topotecan, 9-amino-camptothecin, 9-nitro-camptothecin and 10,11-methylenedioxy-camptothecin; anthracycline derivatives such as doxorubicin, daunorubicin, epirubicin, nemorubicin and idarubicin; podophyllotoxin compounds etoposide and teniposide; anthraquinone derivative like mitoxantrone and losoxantrone; acridine derivatives like amsacrine and actinomaycin D; taxanes such as paclitaxel or docetaxel; vinca alkaloids such as vincristine, vinblastine, vindesine, vinorelbine; estramustine; antifolates such as metotrexate, trimetrexate, tomudex; 5-fluoropyrimidines such as 5-FU, floxuridine, ftorafur and capecitabine; cytidine analogs such as cytarabine, azacitidine and gemcitabine.

With the aim of illustrating the present invention, without posing any limitation to it, the following examples are herewith provided.

EXAMPLE 1

Intravenous Infusion of N-(5-{[(5-{[(5-{[(2-{[amino(imino) methyl] amino}ethyl)amino] carbonyl}-1-methyl-1H-pyrrol-3-yl)amino] carbonyl}-1-methyl-1H-pyrrol-3-yl)amino] carbonyl}-1-methyl-1H-pyrrol-3-yl)-4-[(2-bromo acryloyl) amino]-1-methyl-1H-pyrrole-2-carboxamide Hydrochloride (Internal Code PNU 166196) as a Single Administration Every Three Weeks.

A phase I pharmacological trial was carried out to investigate the iv administration of the title compound given as a single administration every three weeks to patients with solid tumors.

The starting dose of 0.85 mg/m² was initially escalated in an accelerated design (100% dose increase; 1 patient/dose level) and then by a conventional dose escalation in 3-6 patient cohorts. 11 patients have been entered so far and 25 cycles have been evaluated for toxicity at dose levels of 0.85, 1.7, 3.4, 5.1 and 7.5 mg/M². One patient suffering from gastrointestinal sarcoma and treated at the dose level of 5.1 mg/m² has obtained a partial response.

EXAMPLE 2

Intravenous Infusion of N-(5-{[(5-{[(5-{[(2-{[amino(imino) methyl] amino}ethyl)amino]carbonyl}-1-methyl-1H-pyrrol-3-yl)amino] carbonyl}-1-methyl-1H-pyrrol-3-yl)amino]carbonyl}-1-methyl-1H-pyrrol-3-yl)-4-[(2-bromo acryloyl) amino]1-methyl-1H-pyrrole-2-carboxamide Hydrochloride (Internal Code PNU 166196) Administered Weekly for Three Consecutive Weeks Every Four Weeks.

A phase I pharmacological trial was carried out to investigate the iv administration of the title compound given weekly for three consecutive weeks every four weeks to patients with solid tumors.

The starting dose of 0.3 mg/M²/week was initially escalated in an accelerated design (100% dose increase; 1 patient/dose level) and then by a conventional dose escalation in 3-6 patient cohorts. 6 patients have been entered so far and 17 cycles have been evaluated for toxicity at dose levels of 0.3, 0.6, 1.2, 2.4 and 4.8 mg/m²/week.

The invention claimed is:

1. A method of treating tumors in mammals comprising the intravenous infusion to a mammal suffering from a tumor of an α-halogen-acryloyl distamycin derivative as a single administration every three or four weeks in an amount of from 0.85 mg/m² to 20 mg/n² of body surface area, or weekly for three consecutive weeks every four or five weeks in an amount of from 0.3 mg/m²/week to 7 mg/m²/week, wherein said α-halogen-acryloyl distamycin denvative has the formula (I)

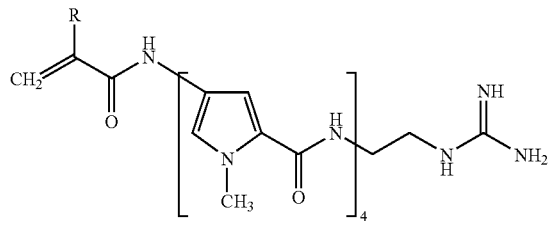

wherein:
R is a bromine or chlorine atom; or a pharmaceutically acceptable salt thereof; and an additional antitumor agent selected from the group consisting of cisplatin, CPT-11 and docetaxel as a combined preparation for simultaneous, separate or sequential use, whereby tumor growth in said mammal is inhibited.

2. The method according to claim 1 wherein said mammal is a human.

* * * * *